(12) United States Patent
Fujisawa

(10) Patent No.: US 8,618,924 B2
(45) Date of Patent: Dec. 31, 2013

(54) TIRE INSPECTION APPARATUS

(75) Inventor: Yoshitaka Fujisawa, Tokyo (JP)

(73) Assignee: Kabushiki Kaisha Bridgestone, Tokyo (JP)

( * ) Notice: Subject to any disclaimer, the term of this patent is extended or adjusted under 35 U.S.C. 154(b) by 196 days.

(21) Appl. No.: 13/320,458

(22) PCT Filed: May 13, 2010

(86) PCT No.: PCT/JP2010/058086
§ 371 (c)(1),
(2), (4) Date: Dec. 8, 2011

(87) PCT Pub. No.: WO2010/131698
PCT Pub. Date: Nov. 18, 2010

(65) Prior Publication Data
US 2012/0092149 A1   Apr. 19, 2012

(30) Foreign Application Priority Data
May 13, 2009   (JP) ................................ 2009-116206

(51) Int. Cl.
  *B60C 23/02*   (2006.01)
(52) U.S. Cl.
  USPC ............................... 340/442; 73/146; 378/61
(58) Field of Classification Search
  USPC ......... 340/442, 443, 444, 445; 73/146, 146.2, 73/146.5; 378/61
  See application file for complete search history.

(56) References Cited

U.S. PATENT DOCUMENTS

| | | | |
|---|---|---|---|
| 5,206,720 A | 4/1993 | Clothiaux et al. | |
| 6,840,097 B1 * | 1/2005 | Huber et al. | 73/146 |
| 7,260,983 B2 * | 8/2007 | Nosekabel et al. | 73/146 |
| 7,360,410 B2 * | 4/2008 | Steinbichler et al. | 73/146 |
| 7,436,504 B2 * | 10/2008 | Shaw et al. | 356/237.2 |
| 8,074,506 B2 * | 12/2011 | Maehner et al. | 73/146 |
| 8,452,072 B2 * | 5/2013 | Sukegawa et al. | 382/141 |

FOREIGN PATENT DOCUMENTS

| | | |
|---|---|---|
| EP | 1 120 640 A1 | 8/2001 |
| JP | A-5-264411 | 10/1993 |
| JP | A-7-152860 | 6/1995 |
| JP | A-2001-249012 | 9/2001 |
| JP | A-2008-185511 | 8/2008 |

OTHER PUBLICATIONS

International Search Report issued in International Patent Application No. PCT/JP2010/058086 dated Jun. 8, 2012 (with translation).

* cited by examiner

*Primary Examiner* — Toan N Pham
(74) *Attorney, Agent, or Firm* — Oliff and Berridge, PLC

(57) ABSTRACT

A tire inspection apparatus arranged with a plurality of cameras located at relatively displaced circumferential positions and set for the respective shooting positions different from each other in the axial direction of the tire. Thus the images of the inner circumferential surface of the tire are shot by the plurality of cameras as the tire is rotated circumferentially relative to the plurality of cameras. During this operation, markers are inserted at the same time in the images shot by all of the cameras. The images are synthesized using these markers as reference positions in aligning the shot images in accordance with the relative displacements of the cameras in the circumferential direction.

9 Claims, 11 Drawing Sheets

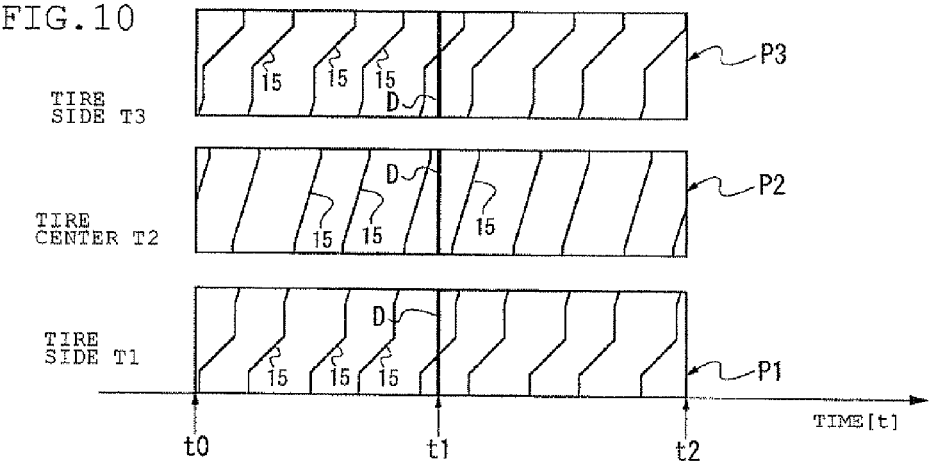
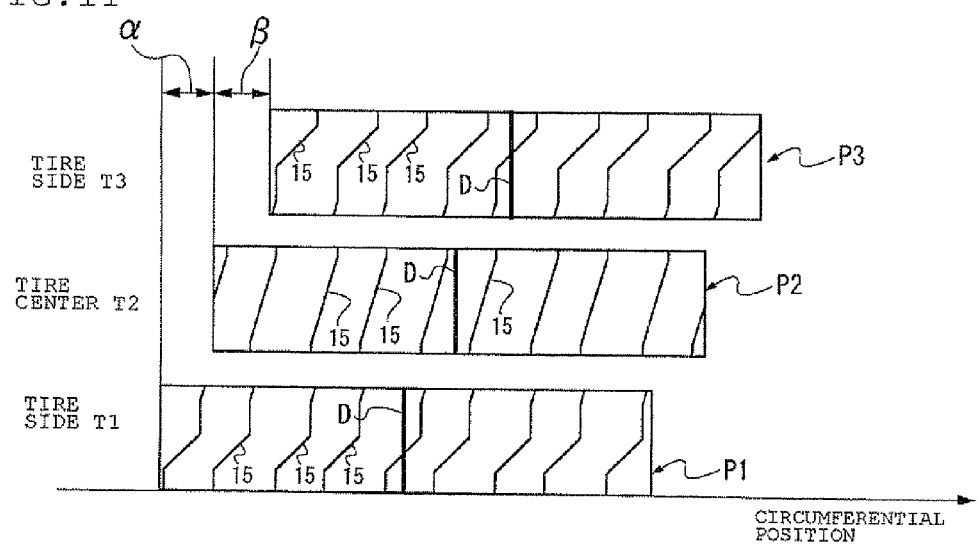
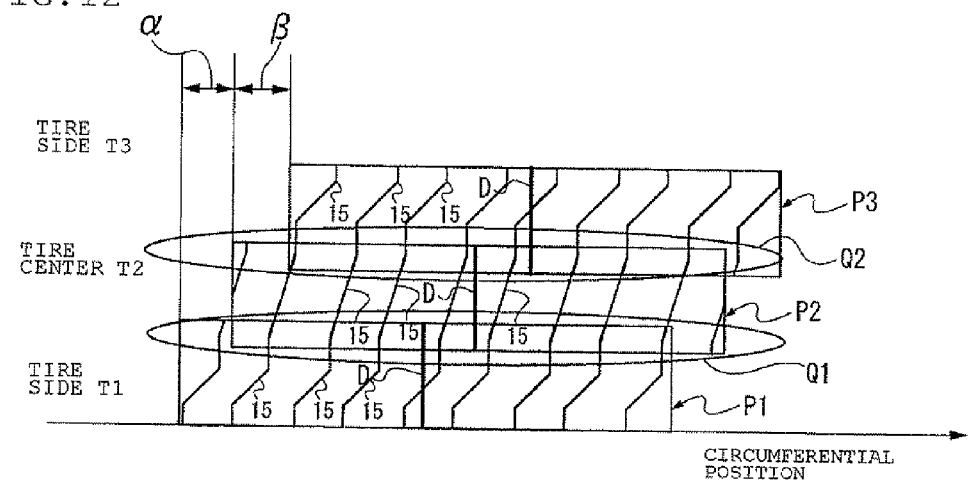

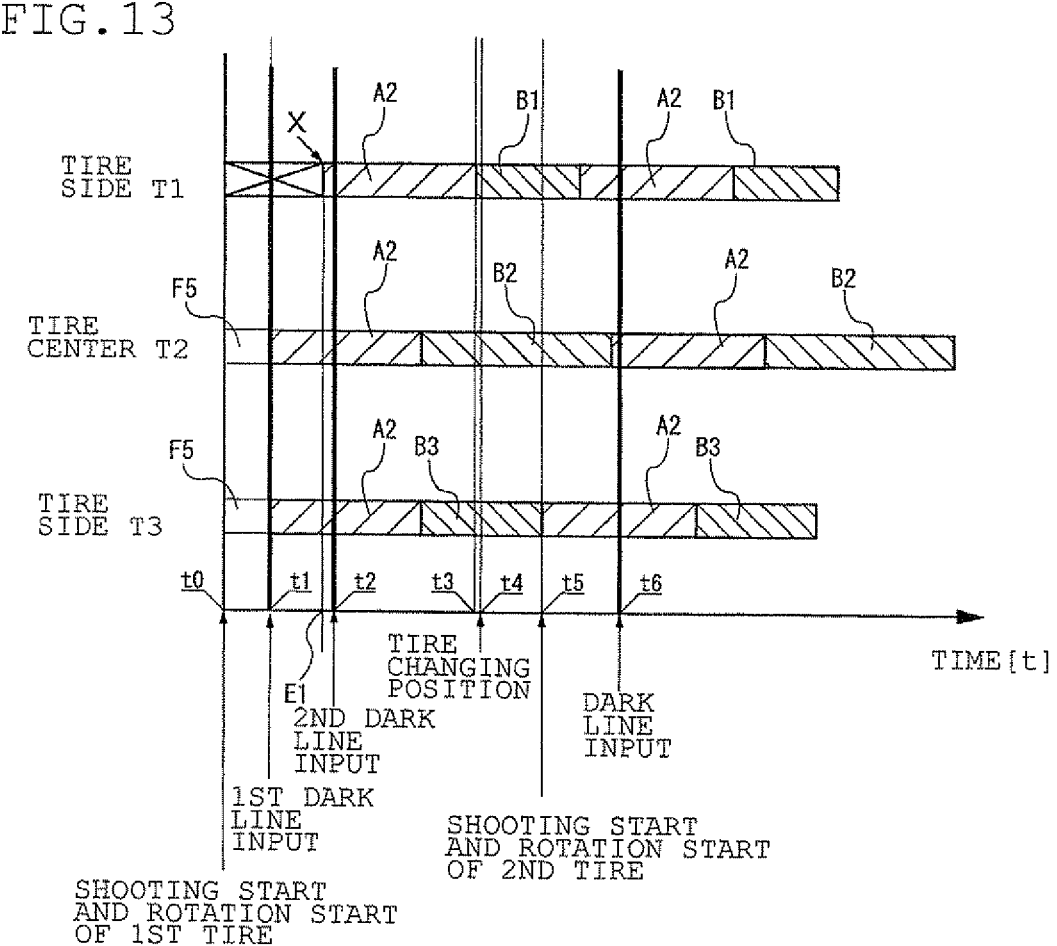

PROCESSING BY 42

ALIGNING BY PATTERN MATCHING

TIRE INSPECTION APPARATUS

TECHNICAL FIELD

The present invention relates to an apparatus for inspecting the appearance of tires. In particular, the invention relates to a tire inspection apparatus for inspecting the inner surface or the outer surface of a tire.

BACKGROUND ART

The appearance inspection of a tire is important in checking for the presence of defects on the tire which has been cure-molded into a product. For example, it is necessary to inspect the inner surface of a tire closely since the defects thereon cannot be visually checked after it is fitted on the wheel.

Conventionally, the tire inner surface Ts has been closely inspected for molding defects and the like, using a tire inspection apparatus as shown in FIG. 14. In carrying out the inspection, cameras 11 to 13 as the image shooting means and laser beam generators 21 to 23 as the illuminating means casting slit light 21a to 23a are disposed in the center opening space of a tire T rotating circumferentially, and the images of portions on the tire inner surface Ts illuminated by the slit light 21a to 23a are shot by the cameras 11 to 13.

For example, three cameras 11 to 13 shooting the images of the inner surface Ts of a tire are set with image shooting orientations such that they can capture the images of different regions, namely, one tire side T1, the tire center T2, and the other tire side T3 of the tire inner surface Ts. Further, since the cameras 11 to 13 are located within the limited space of the tire center opening, the cameras 11 to 13 are so arranged as to have their respective shooting directions relatively displaced from each other circumferentially, as shown in FIG. 15, and also set for the respective shooting positions different from each other in the axial direction of the tire, which is a direction perpendicular to the tire inner circumference. For example, let the shooting direction of the camera 12 be the reference position in the circumferential direction. Then the cameras 11 to 13 may be arranged compactly such that the shooting direction of the camera 11 is displaced by angle α in the circumferentially counterclockwise direction and the shooting direction of the camera 13 is displaced by angle β in the circumferentially clockwise direction.

Laser beam generators 21 to 23 are provided for the cameras 11 to 13, respectively, and they cast slit lights 21a to 23a corresponding to the image shooting orientations. More specifically, the slit lights are cast in the radial directions of the tire such that the slit light 21a cast from the laser beam generator 21 is directed to one tire side T1, the slit light 22a cast from the laser beam generator 22 to the tire center T2, and the slit light 23a cast from the laser beam generator 23 to the other tire side T3. With the cameras 11 to 13 shooting the images of the portions on the tire inner surface Ts illuminated by the slit lights 21a to 23a, the images of surface unevenness, such as defects and mold marks, on the tire inner surface Ts are captured.

The shot image data obtained by the cameras 11 to 13 are outputted to preprocessing means 31 to 33, which are, for instance, computers, connected to the respective cameras. The preprocessing means 31 to 33 perform a preprocessing, which is a processing of the image data, when image shooting for full tire circle or over is completed. As a result of this preprocessing, the shot images P1 to P3 of the respective regions are obtained. The shot images P1 to P3 thus obtained are outputted to the control means 46, which is a computer connected individually to the preprocessing means 31 to 33, whenever a preprocessing is completed.

The control means 46 to which the shot images P1 to P3 are inputted controls the inspection in all aspects, and a keyboard 35 as an input means and a monitor 36 as a display means are connected thereto.

Inputted through the keyboard 35 are information on the size of the tire T to be inspected and the like and the displacement angles α and β for the arrangement of the cameras 11 to 13.

Also, displayed on the monitor 36 are an image synthesized by the image synthesizing means 40 of the control means 46 to be discussed later, an acceptability determination result of the tire T as determined by the acceptability determining means 47, and the like.

The control means 46 is roughly constituted of an image synthesizing means 40, a camera position storage means 44, and an acceptability determining means 47.

The control means 46, which is connected to a motor drive means 51 for controlling the drive of a motor 52 via a drive signal line 70, controls the rotation or the stop of a rotating table 53 which rotates, driven by the motor 52. Further, the control means 46 is connected to the camera 11 and the laser beam generator 21 for shooting the image of the tire side T1 via a shooting signal line 71, to the camera 12 and the laser beam generator 22 for shooting the image of the tire center T2 via a shooting signal line 72, and to the camera 13 and the laser beam generator 23 for shooting the image of the tire side T3 via a shooting signal line 73. Thus, the control means 46 outputs shooting start signals for starting image shooting and shooting end signals for ending image shooting through the respective shooting signal lines 71 to 73.

The camera position storage means 44 stores the relative displacements in the circumferential direction of the cameras 11 to 13, more specifically, the displacement angle α between the cameras 11 and 12 and the displacement angle β between the cameras 12 and 13.

The image synthesizing means 40, which includes a circumferential position aligning means 41, an overlap synthesizing means 42, and a processing means 43, synthesizes the images captured by the cameras 11 to 13.

The circumferential position aligning means 41 reads out the circumferential displacement angles α and β resulting from the arrangement of the cameras 11 to 13 from the camera position storage means 44, shifts the shooting start positions S1 to 83 for the respective images in accordance with the read-out displacements of angles α and β, and align the positions thereof such that it looks as though the cameras 11 to 13 have started shooting simultaneously.

The overlap synthesizing means 42 superimposes the shot images by detecting protruding portions 15 called ridges from the overlap of adjacent images, out of the shot images aligned by the circumferential position aligning means 41, and performing a pattern matching thereof. Note that the "ridges" as used herein are periodically-occurring protruding portions 15 which are formed on the tire inner surface Ts in the process of tire building. They are a transfer of air purge grooves formed at intervals on the surface of the bladder for giving pressure to the tire inner surface Ts in the cure-molding of a tire T.

The processing means 43 processes the images pattern-matched by the overlap synthesizing means 42 into a synthesized image PP for full tire circle before outputting it to the acceptability determining means 47.

The acceptability determining means 47 determines whether there are any tire-building defects or marks on the tire inner surface Ts resulting from cure-molding. This is done by performing an image processing on the surface unevenness of the tire inner surface Ts, using the synthesized image PP synthesized by the processing means 43.

Conventionally, an inspection is carried out as shown in FIG. 16 using an inspection apparatus of a structure as described above.

At time t0, the first tire T for the initial inspection begins rotating as the rotating table 53 rotates at a rotation start signal outputted from the control means 46. At the same time, a shooting start signal is outputted, and slit lights 21a to 23a are cast to the tire sides T1 and T3 and the tire center T2, respectively, from the laser beam generators 21 to 23. And all the cameras 11 to 13 begin shooting the illuminated portions simultaneously. It is to be noted, however, that, relative to the shooting position of the camera 12, the camera 11 begins shooting at a position angle $\alpha$ ahead (phase difference) in the direction of tire rotation G, and the camera 13 at a position angle $\beta$ behind (phase difference) in the direction of tire rotation G. The shot image data obtained by the cameras 11 to 13 are successively outputted to the preprocessing means 31 to 33.

At time t1, when a predetermined shooting time A1, equal to full tire circle or over, has elapsed from the start of shooting at time t0, the control means 46 outputs a rotation stop signal to end the rotation of the tire T to the motor drive means 51 and a shooting end signal to end the shooting to all the cameras 11 to 13 and all the laser beam generators 21 to 23. With the image shooting by all the cameras 11 to 13 completed, the preprocessing means 31 to 33 immediately starts a preprocessing, the procedure of processing the captured image data.

At time t2, after the end of image pickup by all of the cameras 11 to 13 and using the time when the preprocessing means 31 to 33 undertake the preprocessing, the first tire T on the rotating table 53 is replaced by the second tire T to be inspected next. Also, preparation for an immediate start of the next shooting is made by making certain that the cameras 11 to 13 and the laser beam generators 21 to 23 are in predetermined positions within the tire center opening.

Then, at time t3, the preprocessing for the tire side T1 of the first tire is completed in the preprocessing time B1. Next, at time t4, the preprocessing for the tire side T3 is completed in the preprocessing time B3. Finally, at time t5, the preprocessing for the tire center T2 is completed in the preprocessing time B2. Thus the preprocessing for the first tire T is completed. Then the control means 46 performs a control such that all the cameras 11 to 13 start shooting simultaneously with the rotation of the second tire T. At time t6, when the predetermined shooting time A1, equal to full tire circle or over, has elapsed from the start of shooting at time t5, the control means 46 outputs a rotation stop signal to end the rotation of the tire T to the motor drive means 51 and a shooting end signal to end the shooting to all the cameras 11 to 13 and all the laser beam generators 21 to 23. With the image shooting by all the cameras 11 to 13 completed, the preprocessing means 31 to 33 immediately starts a preprocessing, the procedure of processing the shot image data.

At time t7, after the end of shooting by all of the cameras 11 to 13 and using the time when the preprocessing means 31 to 33 undertake the preprocessing, the second tire T on the rotating table 53 is replaced by the third tire T to be inspected next. Also, preparation for an immediate start of the next shooting is made by making certain that the cameras 11 to 13 and the laser beam generators 21 to 23 are in predetermined positions within the tire center opening.

Then, the preprocessing for the tire side T1 of the second tire is completed in the preprocessing time B1. Next, the preprocessing for the tire side T3 is completed in the preprocessing time B3. Finally, at time t8, the preprocessing for the tire center T2 is completed in the preprocessing time B2. Thus the preprocessings for the second tire T are completely finished. By repeating this procedure, the inspections of the tire inner surfaces are carried on successively.

It is to be noted that the differences between the preprocessing times B1, B2, and B3 result from the differences in the size of image shooting range. The preprocessing time B1 is the shortest because the tire side T1 is located on the tire side placed on the table such that the deflection in the tire side T1 disappears, thus making the image shooting range planar. The preprocessing time B3 is the second shortest because the tire side T3 has a rounded image shooting range. The preprocessing time B2 is the longest because the tire center T2 has the widest image shooting range.

The shot images P1 to P3, which have undergone image shooting and preprocessing through the above-described procedures, are outputted individually to the image synthesizing means 40 of the control means 46 immediately after the completion of preprocessing. As soon as the shot images P1 to P3 are all ready, the image synthesizing means 40 carries out a synthesizing process as illustrated in FIGS. 17A to 17D.

Firstly, as shown in FIGS. 17A and 17B, the shooting start positions S1 to S3 of the shot images P1 to P3 are shifted by the circumferential position aligning means 41 by as much as the positional displacement angles $\alpha$ and $\beta$ (phase differences) of the shooting directions of the cameras 11 to 13. More specifically, relative to the shooting start position S2 of the shot image P2, the shooting start position S1 of the shot image P1 is shifted by as much as the angle $\alpha$, and the shooting start position S3 of the shot image 23 is shifted by as much as the angle $\beta$. In this manner, the position alignment is accomplished such that it looks as though all the cameras 11 to 13 have started shooting at the same circumferential position.

Next, as shown in FIG. 17C, the overlaps of the shot images P1 to P3 shot by the cameras 11 to 13 are synthesized by pattern matching by the overlap synthesizing means 42. More specifically, the shot images P1 to P3 are synthesized by pattern-matching the overlap Q1 of the shot images P1 and P2 and the overlap Q2 of the shot images P2 and P3. In the pattern matching, protruding portions 15 formed at intervals in the shot images P1 to P3 are identified therefrom, and then the protruding portions 15 are matched up with each other.

Next, as shown in FIG. 17D, the processing means 43 extracts a synthesized image equal to full tire circle, relative to the shooting start position S3 of the camera 13, by deleting the remaining unnecessary portions. Thus, the images of the tire inner surface Ts for full tire circle are processed as the synthesized image PP. And after the synthesized image PP is checked for acceptability by the acceptability determining means 47, both the synthesized PP and the result of acceptability determination of the tire inner surface Ts resulting from tire building are outputted to the monitor 36 for display.

However, in the structure as described above, the three cameras 11 to 13 are so set as to shoot the images simultaneously as shown in FIG. 15 and FIG. 16. Then, even when the same shooting time A1 is applied to the cameras 11 to 13, the time required for preprocessing will vary with the regions shot if the imaging region of the tire center T2 shot by the camera 12 is wider than the others. As a result, when a preparation is made for the next inspection by placing the next tire T on the rotating table 53 after the end of image shooting by all of the cameras 11 to 13, the cameras 11 and 13 must wait for the completion of preprocessing for the tire center T2. Thus result the waiting times C1 and C2, which can be a waste of time.

For example, the waiting times C1 and C2 are each about 5 or 6 seconds. Yet, a simple calculation on the assumption that about 8,000 tires are inspected per day points to the waiting time of about 11 hours per day. This is an impediment to the improvement of inspection efficiency, and there really exists a need for an efficient method for image shooting and processing.

Also, the shot images P1 to P3 preprocessed by the preprocessing means 31 to 33 are outputted to the control means 46 in nearly the same timing. Hence, there occurs a concentration of load in the network connecting the control means 46 and the preprocessing means 31 to 33. This causes a longer time for transfer of the shot images P1 to P3, which occasionally results in waiting for the transfer or the like. This is also an impediment to smooth performance of inspection of the next tire T.

Further, an inspection by a single session of image shooting does not necessarily result in a successful image shooting of the tire inner surface Ts. There are often image shooting failures, with one of the cameras 11 to 13 developing malfunction. There are even cases of multiple shootings necessitated.

For example, as shown in FIG. 18, if a trouble of image shooting of the tire side T1 (X marked) occurs at time E1 after the start of shooting in the inspection of the first tire T, it will be necessary to carry out the shooting by all of the cameras 11 to 13 again from time E1. Then all the shot image data for the shooting time H on the tire center T2 and the tire side T3 will go to waste.

Moreover, the conventional method for image synthesis is valid when the graphic part for pattern matching is sufficiently large in comparison with the size of the image to be synthesized. Yet, when the protruding portions 15 on the tire inner surface Ts, for instance, are used as the graphic for pattern matching, the interval between the protruding portions 15 is relatively short for the circumferential length of the tire T. As a result, disagreement can often occur in the relationship between the shooting directions of the cameras and the shooting start positions S1 to S3 of the images captured. Thus, if there actually is disagreement between the shooting start positions S1 to S3 and the shooting directions, pattern matching of protruding portions 15 staggered by a single section can occur in the synthesis of the shot images P1 to P3 by the overlap synthesizing means 42 as shown in FIG. 19. Therefore, it is possible that the image of a non-defective tire T is synthesized into an image of a defective tire at the stage of image analysis.

Also, as shown in FIG. 15, the images are synthesized from the shooting start positions S1 to S3 of shot images and the relative displacement angles α and β of the cameras 11 to 13. Hence, it is necessary to carry out shootings for full tire circle or over if shot images for full tire circle are to be obtained with certainty. This means unnecessary portions of time spent in the image shooting time and preprocessing time.

For example, Patent Document 1 discloses a technology of image shooting by CCD cameras, which are a plurality of image shooting means arranged with circumferential position displacements, while slit lights are cast to the tire inner surface.

According to the method of Patent Document 1, however, the inspection of the tire inner surface is performed by comparing the images of individual regions shot by the plurality of image shooting means against the master images of the tire inner surface prepared in advance. This requires extra trouble since the master images of the tire inner surface to be inspected must be prepared in advance. Also, tires having undergone the tire-building process have individual differences on the tire inner surface such that comparison with the master images cannot assure accurate inspection of the tire inner surface because of the individual differences.

Also, Patent Document 2 discloses a technology for image processing through pattern matching of shot images. In this technology of judging raised letter information through pattern matching, raised letters formed on the tire side at the time of cure-molding, for instance, are shot with a camera, the raised letters are read by a processing means from the shot image, and the raised letters are compared with a master image stored in the processing means in advance.

PRIOR ART DOCUMENT

Patent Document

Patent Document 1: Japanese Unexamined Patent Application Publication No. 2001-249012
Patent Document 2: Japanese Unexamined Patent Application Publication No. 7-152860

SUMMARY OF THE INVENTION

Problem to be Solved by the Invention

The present invention has been made to solve the above-described problems, and an object thereof is to provide a tire appearance inspection apparatus capable of performing appearance inspection of the inner surface or the outer surface of a tire, for instance, in shortened processing time by efficiently shooting the images of the tire and accurately synthesizing the images shot.

Means for Solving the Problem

In a first aspect of the present invention, a tire appearance inspection apparatus includes a plurality of image shooting means located at positions relatively displaced in the circumferential direction so as to shoot images of the circumferential surface of a tire and set for the respective imaging positions different from each other in the axial direction of the tire, a marker inserting means for entering markers in the images shot by all of the image shooting means at the same time when image shooting is being performed by all of the image shooting means while the tire is rotated circumferentially relative to the plurality of image shooting means, and an image synthesizing means for synthesizing the images shot by all of the image shooting means by shifting the markers in accordance with the relative displacements in the circumferential direction of the respective image shooting means.

According to the invention, the marker inserting means enters markers in the images shot by all of the image shooting means at the same time. Thus, all the shot images can be synthesized using the markers as a reference, without starting the shooting by the plurality of image shooting means simultaneously. This arrangement, without the need to perform the image shooting by the plurality of image shooting means simultaneously, can realize inspection based on efficient image shooting.

In a second aspect of the present invention, the tire inspection apparatus is so arranged that the image shooting operation of the image shooting means is started one after the other as an image data processing operation after an image shooting operation is finished.

According to the invention, the image shooting by the image shooting means can be started one after the other as an image data processing operation after an image shooting operation is finished. Therefore, the image shooting operations can be performed continuously, and the inspection can be carried out with great efficiency.

In a third aspect of the present invention, the tire inspection apparatus is so arranged that the image shooting operation of the image shooting means is started in timings different for the respective image shooting means.

According to the invention, it is not required that the image shooting means perform the shooting simultaneously. Hence, the image shooting can be carried on without waiting for the end of shooting by the last of the plurality of image shooting means. Thus, the image shooting means can perform image shooting efficiently.

In a fourth aspect of the present invention, the tire inspection apparatus is so arranged that changing of the tire to be inspected is performed after the completion of image shooting by all of the image shooting means.

According to the invention, the tire can be replaced with the next one to be inspected as soon as the image shooting operation by all of the image shooting means is completed. Thus the tire change can be made without waiting for the end of the image data processing operation. Therefore, the image shooting means can start shooting immediately in order of finish of shot data processing, thus raising the efficiency of inspection.

In a fifth aspect of the present invention, the tire inspection apparatus is so arranged that the marker inserting means causes a change in luminance of the illuminating means illuminating the shooting positions of the respective image shooting means.

According to the invention, a change in luminance of the illuminating means is used as the marker, so that the control is easy without the need for other arrangements. For example, the luminance can be changed to zero. This can create a clear difference in luminance from the shot images, thus allowing easy detection of marker positions.

In a sixth aspect of the present invention, the tire inspection apparatus is so arranged that the marker inserting means creates noise in the images shot by the respective image shooting means.

According to the invention, an image apparently different from the other parts is inserted among the shot images, so that detection of marker positions becomes easy.

In a seventh aspect of the present invention, the tire inspection apparatus is so arranged that the marker inserted by the marker inserting means consists of a plurality of lines.

According to the invention, a marker consisting of a plurality of lines is inserted at the same time such that markers on the same pattern are inserted in all of the shot images. This makes detection of marker positions easier.

In an eighth aspect of the present invention, the tire inspection apparatus is so arranged that the image shooting means perform image shootings of a circumferential surface of the tire for full circle and an image shooting of a marker inserted only.

According to the invention, the image shooting means do not perform more than necessary image shootings. Therefore, the time for image pickup and the time for processing the shot image data will be shorter.

In a ninth aspect of the present invention, the tire inspection apparatus is so arranged that the plurality of image shooting means are so set as to shoot the respectively different regions of a tire circumferential surface and the image shooting means shooting the neighboring regions capture images such as to have overlaps of the regions, so that the images can be synthesized by performing pattern matching of the overlaps of the images shot.

According to the invention, the neighboring regions are shot by the image shooting means such as to have overlaps. Thus the shot images captured by a plurality of image shooting means can be synthesized by pattern matching, which makes the image synthesis easy.

BRIEF DESCRIPTION OF THE DRAWINGS

FIG. 10 is a diagram showing shot images with dark lines inserted in accordance with a second embodiment of the present invention.

FIG. 11 is a conceptual diagram of circumferential position alignment of shot images using dark lines in accordance with a second embodiment of the present invention.

FIG. 12 is a conceptual diagram of synthesis of shot images by pattern matching in accordance with a second embodiment of the present invention.

FIG. 13 is a time-series processing diagram for correcting a shooting error in a tire inner surface inspection in accordance with a second embodiment of the present invention.

FIG. 15 is a conventional time-series processing diagram of a tire inner surface inspection.

BEST MODE FOR CARRYING OUT THE INVENTION

First Embodiment

Figure 1:
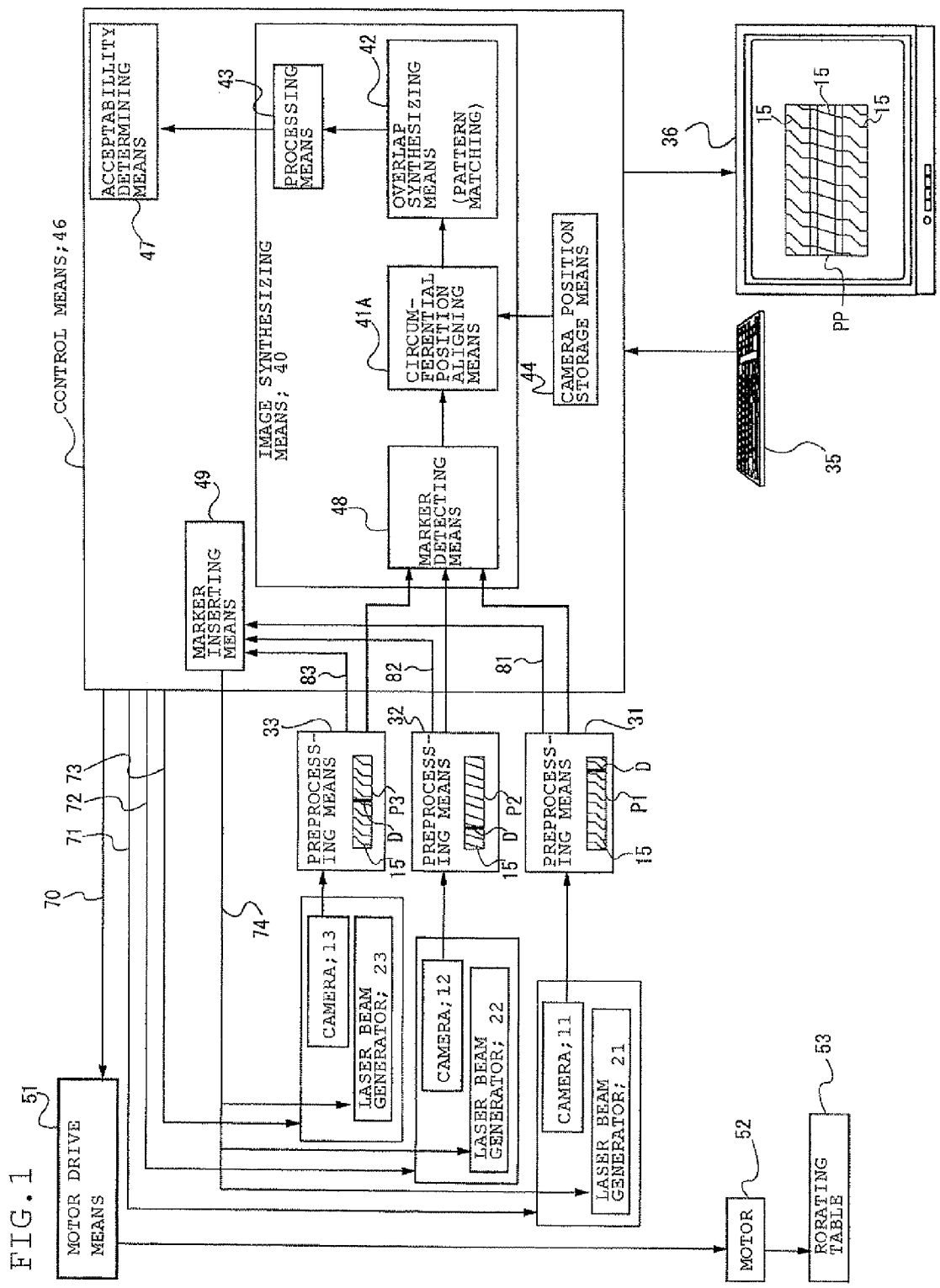
FIG. 1 is a block diagram of an appearance inspection apparatus for inspecting the inner surface of a tire in accordance with a first embodiment of the present invention.
Figure 2:
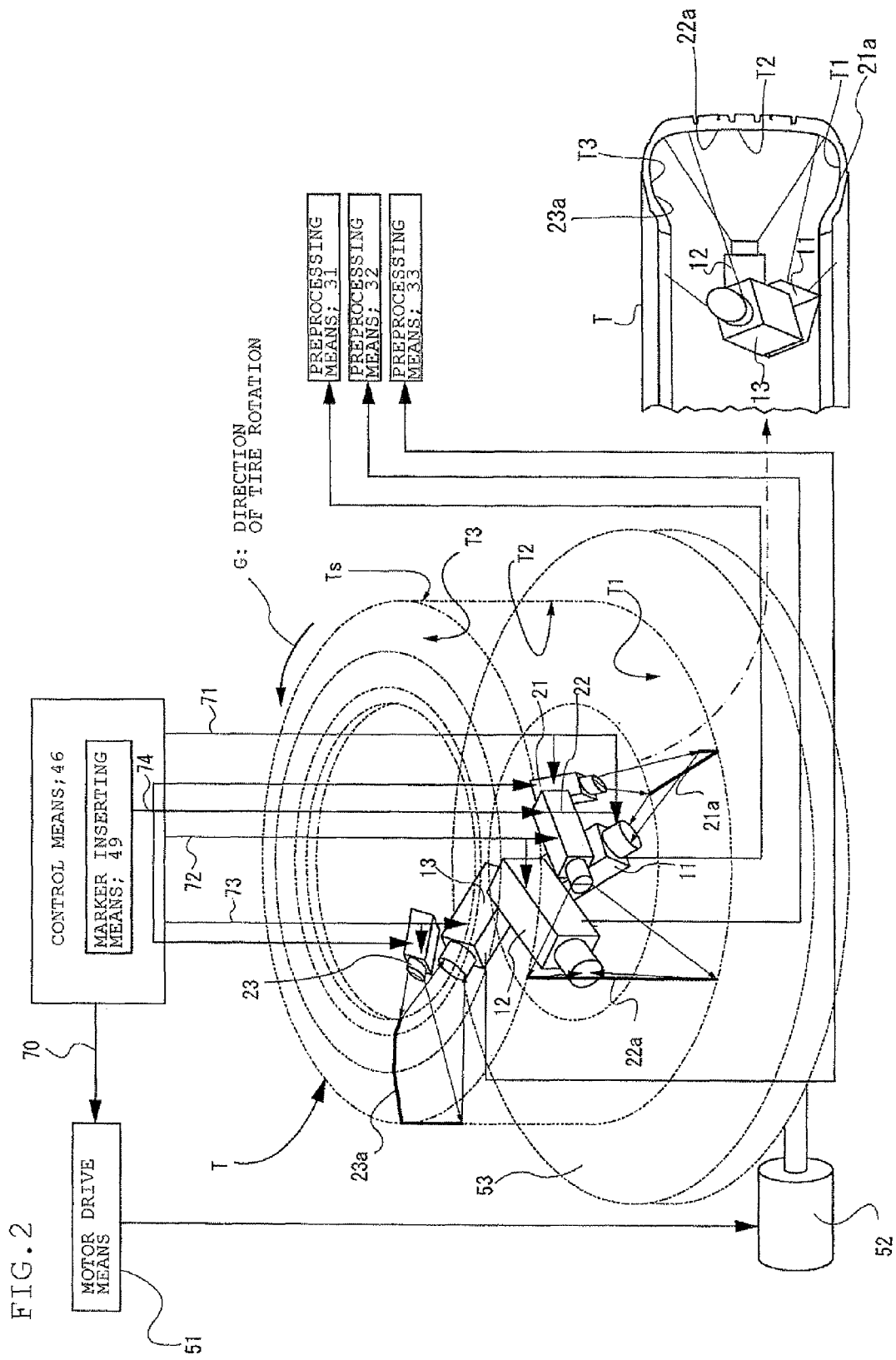
FIG. 2 is an enlarged illustration of an appearance inspection apparatus for inspecting the inner surface of a tire in accordance with a first embodiment of the present invention.
Figure 14:
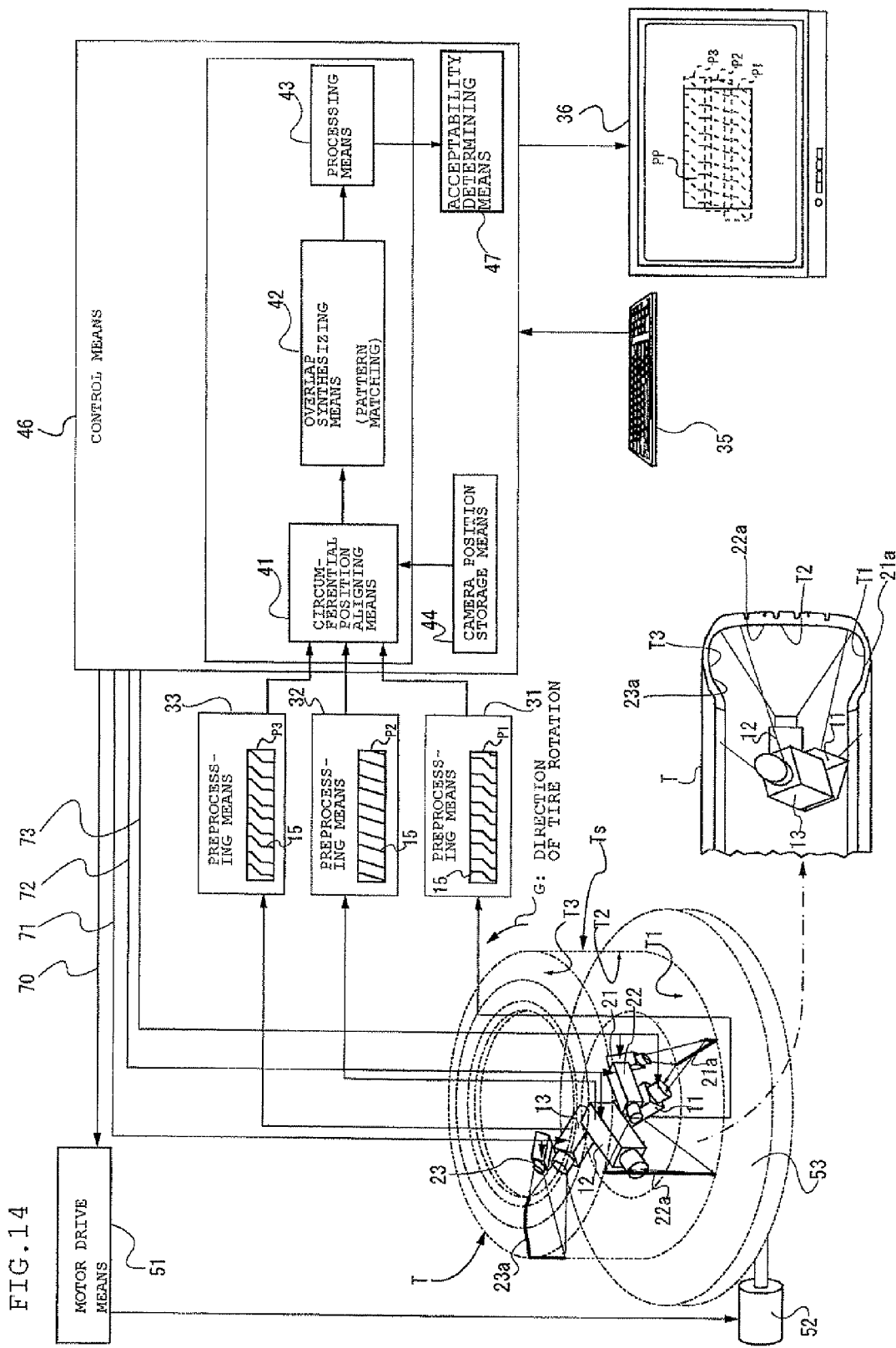
FIG. 14 is a schematic block diagram of a conventional appearance inspection apparatus for inspecting the inner surface of a tire.

FIG. 1 is a block diagram showing a preferred embodiment in which a tire inspection apparatus according to the present invention is applied to the inspection of the tire inner surface Ts of the circumferential surfaces of a tire to be inspected. FIG. 2 is an enlarged illustration of an inspection apparatus which is represented in a block diagram in FIG. 1. Note that, in FIGS. 1 and 2, the identical reference numerals are given to the identical components found in FIG. 14.

As shown in FIGS. 1 and 2, a tire T, which is an object to be inspected, is placed on its side on a rotating table 53 in such a manner that the center of the tire T is aligned with the center axis of the rotating table 53. Driven by a motor 52, the rotating table 53 rotates in the direction of arrow G. In the center opening area of the tire T, a not-shown suspension member is installed vertically from above the tire T. And mounted to the end of the suspension member are laser beam generators 21 to 23, which are illuminating means casting slit lights 21a to 23a to the tire inner surface Ts, and a plurality of cameras 11 to 13, which are CCD area cameras as image shooting means shooting the portions illuminated by the slit lights 21a to 23a.

For image shooting (image pickup), the tire inner surface Ts is divided into three regions, namely, the tire side T1, which is the lower surface, the tire center T2, which is the bottom surface, and the tire side T3, which is the upper surface. The tire side T1 is shot by the laser beam generator 21 and the camera 11, the tire center T2 by the laser beam generator 22 and the camera 12, and the tire side T3 by the laser beam generator 22 and the camera 13, respectively.

Figure 15:
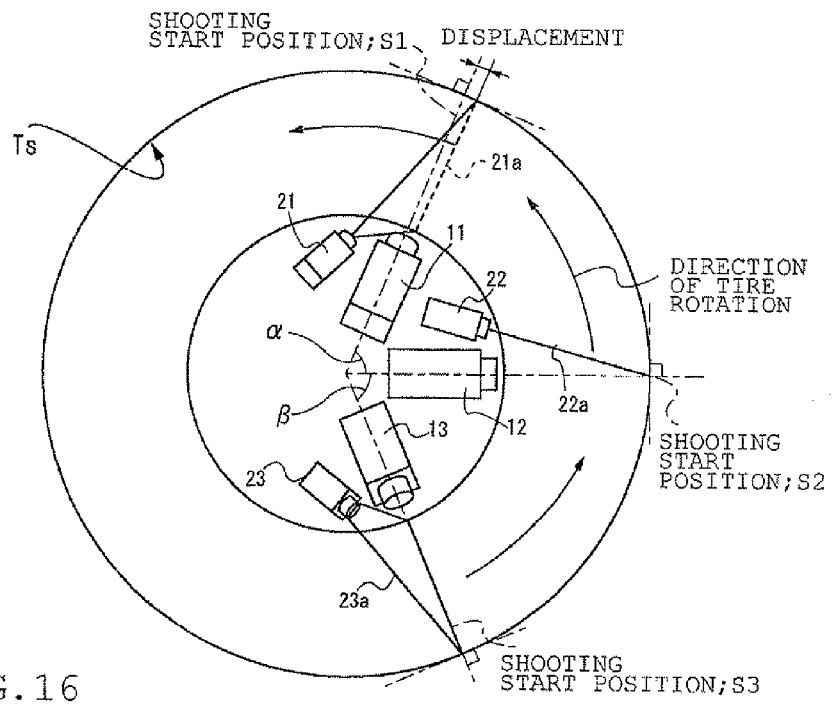
FIG. 15 is a conventional arrangement plan of cameras and laser beam generators.
Figure 16:
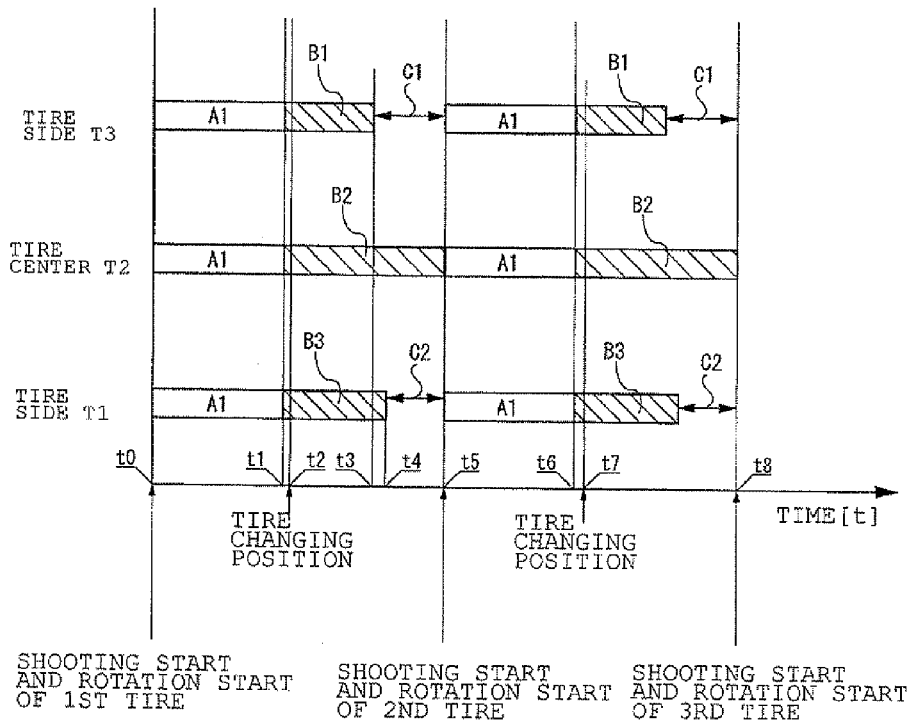
Figure 17:
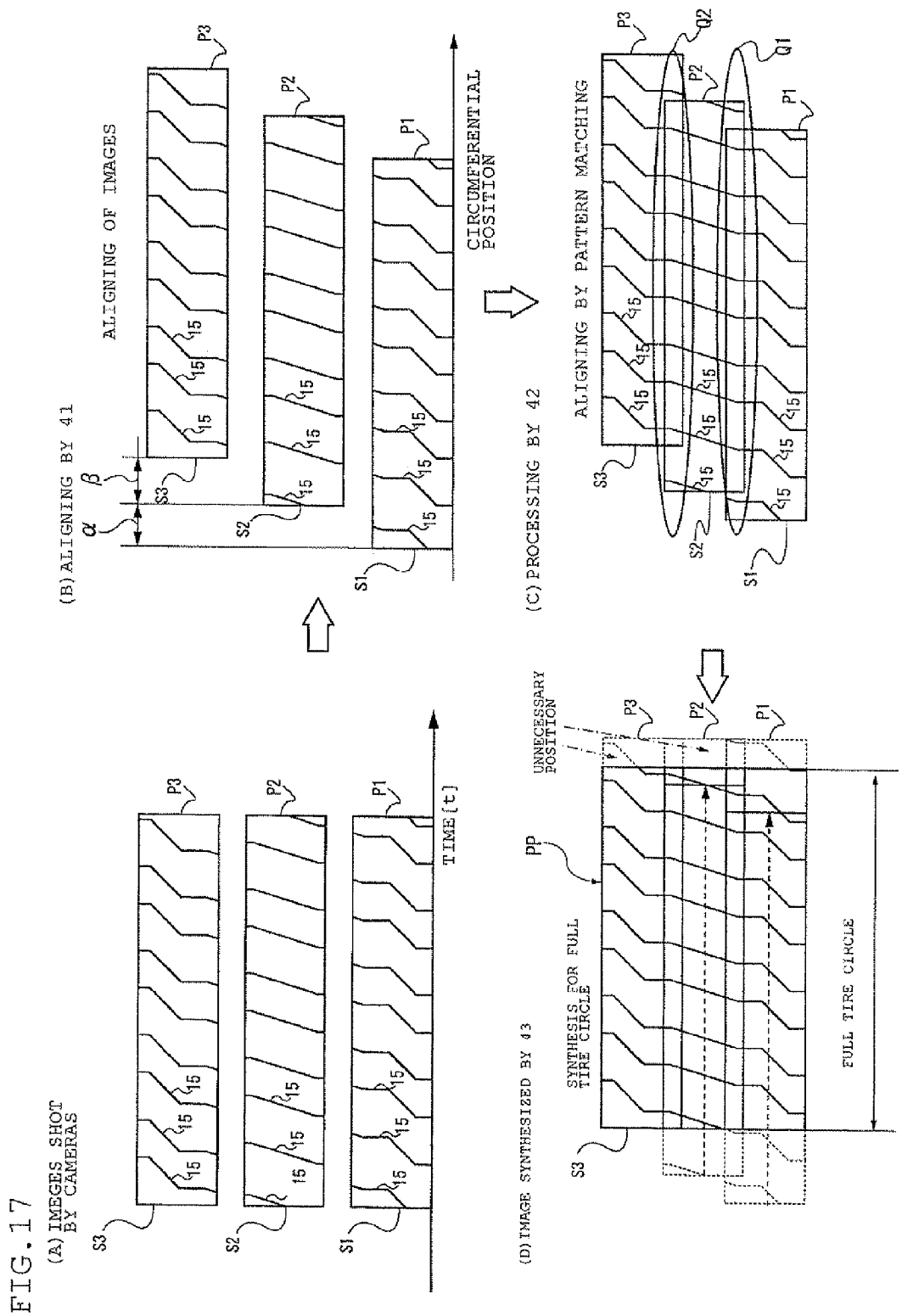
FIG. 17 is a conventional conceptual diagram of synthesis of shot images for respective regions.
Figure 18:
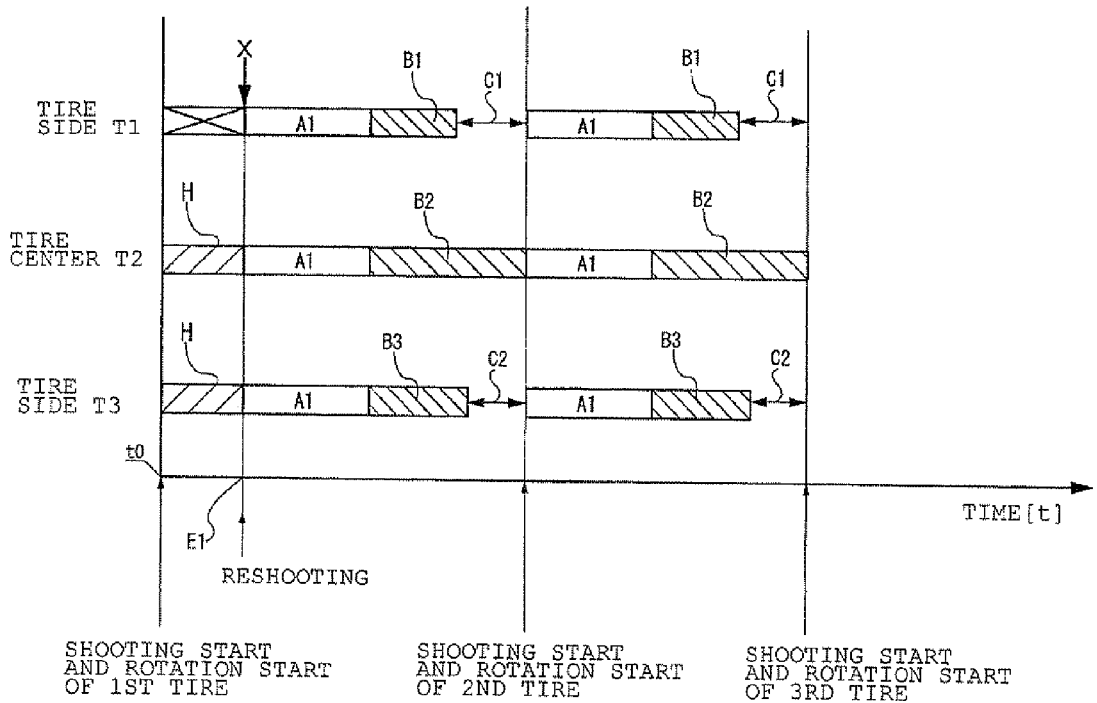
FIG. 18 is a conventional time-series processing diagram for correcting a shooting error in a tire inner surface inspection.
Figure 19:
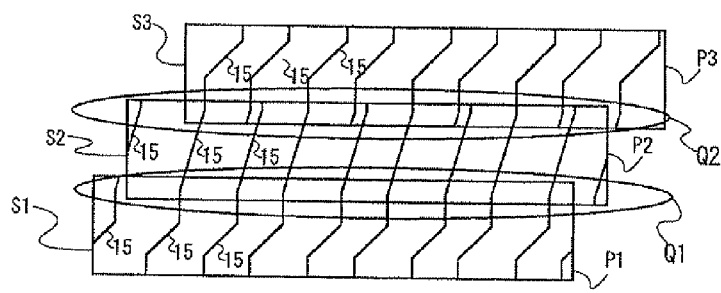
FIG. 19 is a diagram showing mismatching in a conventional image synthesis.

For example, relative to the camera 12 whose shooting direction faces directly the inner circumferential surface of the tire center T2, the camera 11 is oriented toward a position which is angle α ahead in the direction of tire rotation indicated by arrow G. Also, the camera 13 is oriented toward a position which is angle β behind in the direction of tire rotation indicated by arrow G. In other words, the cameras 11 to 13, as shown in FIG. 15, are so arranged with relative displacements in the circumferential direction and also set for the respective imaging positions different from each other in the axial direction of the tire, which is a direction perpendicular to the tire inner circumference. And slit lights 21a to 23a are cast from the laser beam generators 21 to 23 in a manner corresponding to the shooting directions of the cameras 11 to 13, respectively.

It should be understood that the angle α and the angle β for the relative displacements of the cameras 11 to 13 in the circumferential direction may be determined as appropriate. For example, they may be set in any way provided that the cameras can be disposed within the center opening area of the tire T and the images of the tire inner surface Ts can be shot by them.

The shot image data obtained by all the cameras 11 to 13 are successively outputted to preprocessing means 31 to 33, which are computers or the like connected to the cameras 11 to 13, respectively. The images of the regions (T1, T2, T3) for which the shooting is completed are respectively subjected to a preprocessing, such as filtering, by the preprocessing means 31 to 33. The shot images P1 to P3 after the preprocessing are individually outputted to an image synthesizing means 40 of a control means 46 to be discussed later, which is connected to the preprocessing means 31 to 33.

The control means 46 to which the shot images P1 to P3 are outputted controls the inspection in all aspects. The control means 46 is roughly constituted of an image synthesizing means 40, a camera position storage means 44, an acceptability determining means 47, and a marker inserting means 49 which has to do with the present invention. And further connected thereto are a keyboard 35 as an input means and a monitor 36 as a display means.

The control means 46, which is connected to a motor drive means 51 via a drive signal line 70, outputs a rotation start signal or a rotation end signal to control the rotation or stopping of a rotating table 53 by driving a motor 52 via the drive signal line 70.

Also, the control means 46 is connected to the camera 11 and the laser beam generator 21 for shooting the image of the tire side T1 via a shooting signal line 71, to the camera 12 and the laser beam generator 22 for shooting the image of the tire center T2 via a shooting signal line 72, and to the camera 13 and the laser beam generator 23 for shooting the image of the tire side T3 via a shooting signal line 73. Thus, the control means 46 outputs shooting start signals and shooting end signals through the respective shooting signal lines 71 to 73.

In other words, the control means 46 controls the shooting by the camera 11, the shooting by the camera 12, and the shooting by the camera 13 individually, so that their respective shootings are started and stopped at optional positions for the rotating tire T.

Also, the control means 46 outputs a shooting start signal to each of the cameras 11 to 13 and then counts the number of shootings by each of the cameras 11 to 13 individually. And when the number of shootings by each of the cameras 11 to 13 reaches the number of shootings per full tire circle plus one time of shooting for the insertion of a dark line D, the control means 46 outputs a shooting end signal to each of the cameras 11 to 13 individually.

Figure 3:
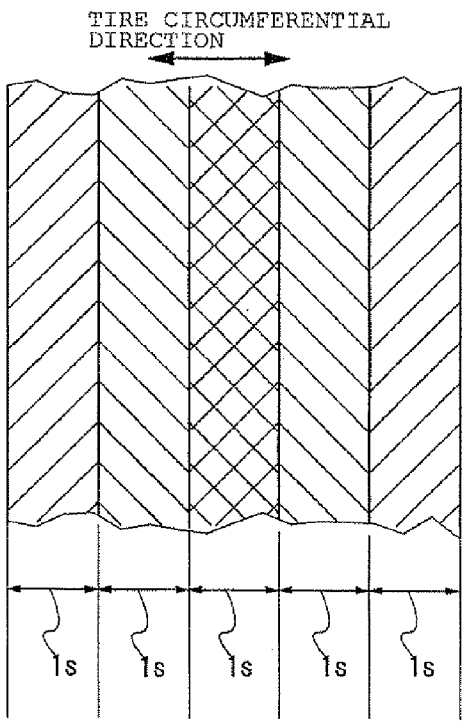
FIG. 3 is a conceptual diagram showing the slit width and the number of image shootings for the inner surface of a tire in accordance with a first embodiment of the present invention.

A description will now be given of the number of shootings. FIG. 3 shows a concept of shot images of the tire center T2. In the figure, 1s represents the slit width of the slit lights 21a to 23a, and the images in the circumferential direction of the tire inner surface Ts can be obtained continuously by shooting full circle of the tire T using this slit width 1s. Therefore, if the tire T to be shot is large, the number of shootings will be proportionately large. And if the tire to be shot is small, the number of shootings will be proportionately small.

Also, the counting of the number of shootings is done as follows. The counting is started at the start of image shooting, and the count is reset at the input of a dark line D as the marker. The counting is resumed from the insertion of the dark line D and comes to an end when the number of shootings for full tire circle plus one time of shooting is reached. Also, for example, when some shooting error occurs, the count of the number of shootings for the camera that has developed the error is reset, and the counting is performed all over again. At this time, a reinsertion signal of a dark line D is outputted to the marker inserting means 49 to be discussed later. Accordingly, a dark line D is again inserted in all the shot images, and a recounting is performed.

In other words, the shot images for full tire circle can be obtained by always capturing images for the "number of shootings for full tire circle+one time of shooting" continuously.

Annunciation signals indicating shooting in progress, end of preprocessing, etc., which are outputted individually from the preprocessing means 31 to 33, are inputted to the control means 46. The control means 46 and the preprocessing means 31 are connected by an annunciation signal line 81, the control means 46 and the preprocessing means 33 by an annunciation signal line 82, and the control means 46 and the preprocessing means 33 by an annunciation signal line 83, respectively.

The marker inserting means 49 is connected to the laser beam generators 21 to 23 by a marker insertion line 74. When an annunciation signal of shooting in progress is outputted from all of the preprocessing means 31 to 33 to the control means 46, the control means 46 performs a control to change the luminance of the slit lights 21a to 23a for a length of one shooting.

More specifically, a control is performed by outputting a marker insertion signal simultaneously to the laser beam generators 21 to 23 via the marker insertion line 74, so that the slit lights 21a to 23a are turned off for a length of one time of shooting. Thus, a dark line D as the marker is inserted in the images captured by the cameras 11 to 13.

The camera position storage means 44 stores the relative displacements in the circumferential direction of the shooting directions of the cameras 11 to 13 as the angles. Relative to the position of the camera 12, the camera position storage means 44 stores the displacement between the camera 11 and the camera 12 as angle α and the displacement between the camera 12 and the camera 13 as angle β.

The image synthesizing means 40 includes a marker detecting means 48, a circumferential position aligning means 41A, an overlap synthesizing means 42, and a processing means 43.

The marker detecting means 48 detects the positions of the dark lines D in the shot images P1 to P3 inputted from the preprocessing means 31 to 33.

The circumferential position aligning means 41A reads out the circumferential displacement angles α and β resulting from the arrangement of the cameras 11 to 13 from the camera position storage means 44, and shifts the dark lines D in the shot images P1 to P3 detected by the marker detecting means 48 in accordance with the angles α and β. In this manner, alignment can be accomplished as if the cameras 11 to 13 have started image shooting simultaneously.

The overlap synthesizing means 42 detects protruding portions 15 from the shot images P1 to P3 aligned with each other by the circumferential position aligning means 41A and synthesizes them through a pattern matching using the protruding portions 15.

The processing means 43 processes the images pattern-matched by the overlap synthesizing means 42 into a synthesized image PP for full tire circle. This synthesized image PP is outputted to the acceptability determining means 47. The acceptability determining means 47 determines whether there are any tire-building defects or marks on the tire inner surface Ts resulting from cure-molding by performing an image processing on the surface unevenness in the synthesized image PP. The synthesis of the images by the image synthesizing means 40 will be described in detail later.

Figure 4:
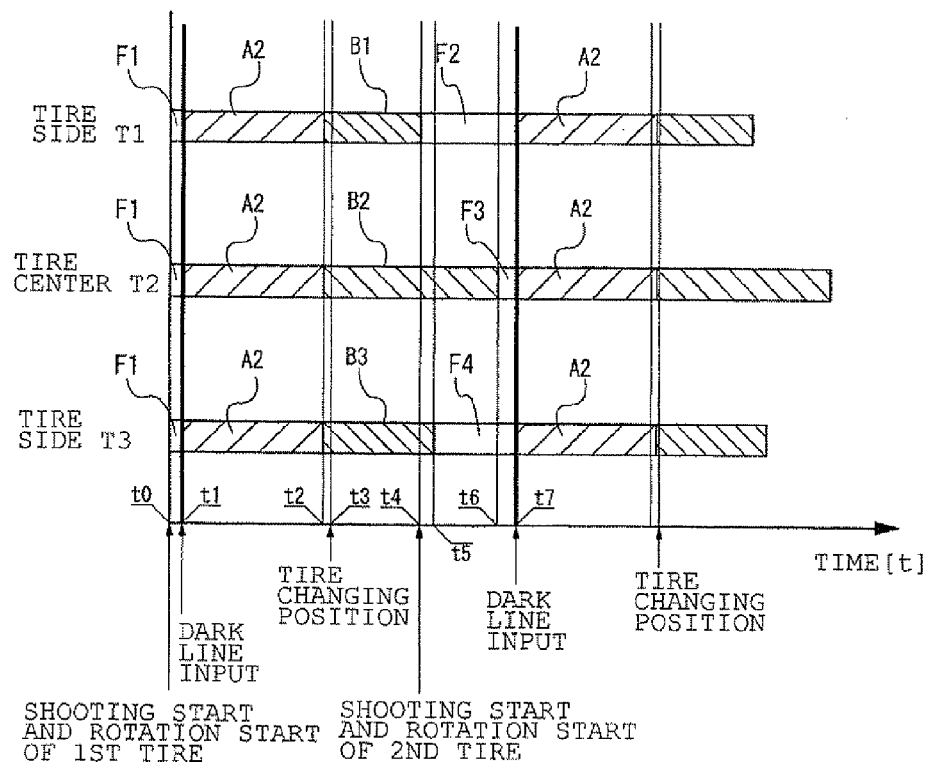
FIG. 4 is a time-series processing diagram of a tire inner surface inspection in accordance with a first embodiment of the present invention.

By implementing the structure as described above, in inspection of the tire inner surface Ts is carried out as shown in FIG. 4. FIG. 4 shows a time-series processing of image shooting and preprocessing in an inspection of the tire inner surface. A description will be given of the inspection processes of the tire inner surface Ts according to this arrangement by referring to this figure. Note that A2 in the figure refers to an image shooting time equal to "number of shootings for full tire circle+one time of shooting".

Firstly, as a preparatory step for the inspection, a person in charge of this inspection places a first tire T to be inspected on the rotating table 53. Then he/she enters information on the size and the like of this tire T and the angles α and β as the relative displacements of the cameras 11 to 13 through the keyboard 35. This causes the control means 46 to calculate the number of shootings appropriate for the size of the tire T.

Next, the inspector locates the cameras 11 to 13 and the laser beam generators 21 to 23 in their predetermined positions within the center opening of the tire T, so that the shooting center of the camera 12, for instance, is approximately in agreement with the axial center position of the tire T. It should be noted that the arrangement may be such that the control means 46 automatically controls the vertical movement of the not-shown suspension member to set them in the predetermined positions according to the size of the tire T inputted through the keyboard 35.

With an input of inspection start from the keyboard 35 after the location of the cameras 11 to 13 is completed, an inspection start signal is inputted to the control means 46.

In FIG. 4, at time t0, with the input of an inspection start signal, the first tire T in this inspection begins rotating, and at the same time the cameras 11 to 13 begin their image pickup. Since this is the initial image shooting for the first tire of the inspection, the image shootings of the respective regions, namely, the tire side T1, the tire center T2, and the tire side T3, are started simultaneously. With the start of these image shootings, the control means 46 starts counting the number of shootings by each of the cameras 11 to 13 individually. Note that during the image shooting, the slit lights 21a to 23a are cast continuously at the tire inner surface Ts which is rotating.

The image data obtained by the cameras 11 to 13 are successively outputted to the preprocessing means 31 to 33. And as the image data are inputted to the preprocessing means 31 to 33, an annunciation signal indicating the image shooting in progress by each of the cameras 11 to 13 is outputted individually from the preprocessing means 31 to 33 to the control means 46.

Next, at time t1, when all the annunciation signals indicating the image shooting in progress outputted individually from the preprocessing means 31 to 33 have been inputted to the control means 46, the marker inserting means 49 of the control means 46 outputs a marker insertion signal to the laser beam generators 21 to 23 so that the slit lights 21a to 23a are turned off simultaneously for a time length equal to a single shooting. This results in an image of a pitch-dark marker of the same time, that is, a dark line D, within the images shot by the cameras 11 to 13.

With the dark lines D inserted, the control means 46 resets the numbers of shootings by the cameras 11 to 13 thus far counted, and starts counting the respective numbers of shootings by the cameras 11 to 13 again.

At this time, it is so arranged that the image data obtained during the image shooting time F1 between time t0 and time t1 are overwritten with the image data obtained after the insertion of the dark lines D.

Next, at time t2, the number of shootings by each of the cameras 11 to 13 since the insertion of the dark lines D at time t1 reaches the predetermined "number of shootings for full tire circle+one time of shooting" in the image shooting time A2. Therefore, the image shooting operation of all the cameras 11 to will come to an end, and at the same time, the preprocessing means 31 to 33 will start the operation of processing (preprocessing) the image data.

Next, at time t3, the image shooting operation by all the cameras 11 to 13 is already finished. Hence, the second tire T to be inspected next is placed on the rotating table 53, and the start of image shooting is waited for.

Then, at time t4, the preprocessing means 31, when it completes the preprocessing for the tire side T1 of the first tire in the preprocessing time B1, outputs an annunciation signal indicating the end of preprocessing to the control means 46. Now the control means 46, based on this annunciation signal, causes not only the second tire T to rotate but also the camera 11 to start shooting the tire side T1 of the second tire, and starts counting the number of shootings. As the image data resulting from the start of image shooting by the camera 11 is outputted to the preprocessing means 31, the preprocessing means 31 outputs an annunciation signal indicating the shooting in progress by the camera 11 to the control means 46.

Next, at time t5, the preprocessing means 33, when it completes the preprocessing for the tire side T3 of the first tire in the preprocessing time B3, outputs an annunciation signal indicating the end of preprocessing to the control means 46. The control means 46, in turn, causes the camera 13 to start shooting the tire side T3 of the second tire from an arbitrary position of the rotating tire T and starts counting the number of shootings. As the image data resulting from the start of image shooting by the camera 13 is outputted to the preprocessing means 33, the preprocessing means 33 outputs an annunciation signal indicating the shooting in progress by the camera 13 to the control means 46.

Next, at time t6, the preprocessing means 32, when it completes the preprocessing for the tire center T2 of the first tire in the preprocessing time B2, outputs an annunciation signal indicating the end of preprocessing to the control means 46. The control means 46, in turn, causes the camera 12 to start shooting the tire center T2 of the second tire from an arbitrary position of the rotating tire T and starts counting the number of shootings. As the image data resulting from the start of image shooting by the camera 12 is outputted to the preprocessing means 32, the preprocessing means 32 outputs an annunciation signal indicating the shooting in progress by the camera 12 to the control means 46. With this annunciation signal from the preprocessing means 32 inputted to the control means 46, the control means 46 is notified of the fact that the image shooting of the second tire T by all of the cameras 11 to 13 has started.

Next, at time t7, based on the above annunciation signal, the marker inserting means 49 of the control means 46 outputs a marker insertion signal to the laser beam generators 21 to 23 so that the slit lights 21a to 23a are turned off simultaneously for a time length equal to a single shooting. This results in an image of a dark line D as the marker of the same time within each of the images shot by the cameras 11 to 13.

With the dark lines D inserted, the control means 46 resets the numbers of shootings by the cameras 11 to 13 thus far counted, and starts counting the respective numbers of shootings by the cameras 11 to 13 again.

At this time, it is so arranged that the image data obtained by the camera 11 during the image shooting time F2 between time t4 and time t5 are overwritten with the image data obtained after the insertion of the dark line D; the image data obtained by the camera 13 during the image shooting time F4 between time t5 and time t6, with the image data obtained after the insertion of the dark line D; and the image data obtained by the camera 12 during the image shooting time F3 between time t6 and time t7, with the image data obtained after the insertion of the dark line D.

Thus, an inner surface inspection of the tire T is carried on successively by repeating the procedure as described above.

Figure 5:
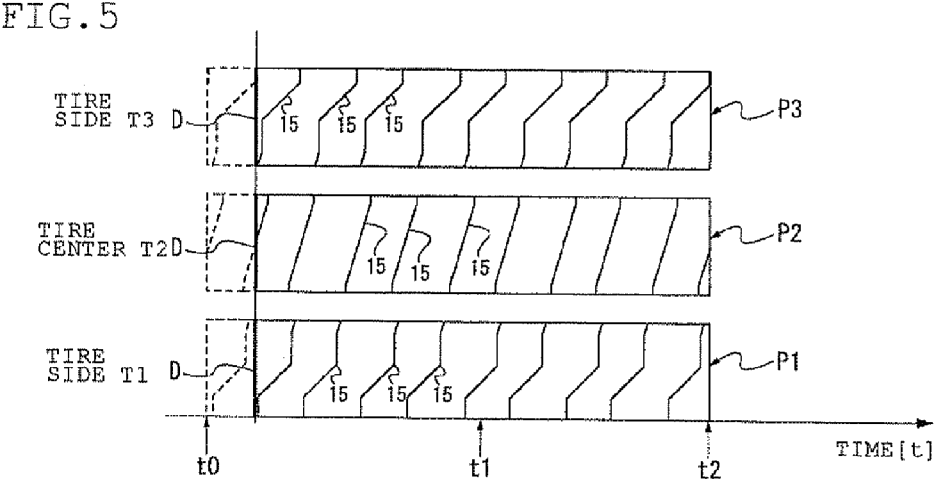
FIG. 5 is a diagram showing shot images with dark lines inserted in accordance with a first embodiment of the present invention.
Figure 6:
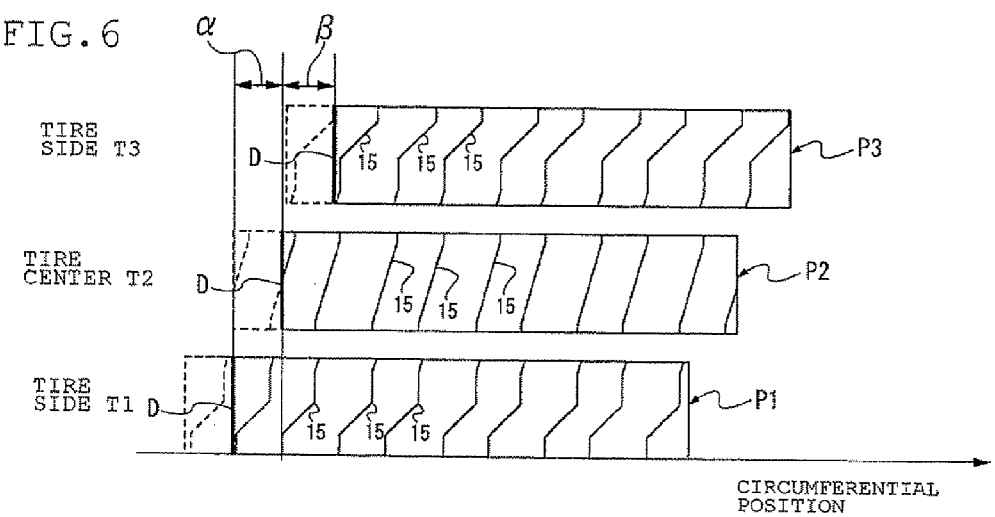
FIG. 6 is a conceptual diagram of circumferential position alignment of shot images using dark lines in accordance with a first embodiment of the present invention.

FIGS. 5 to 9 show a synthesis procedure for synthesizing the shot images P1 to P3 having undergone image shooting and preprocessing in the preceding processes by the image synthesizing means 40. A description will now be given of the synthesis procedure for the shot images P1 to P3 by the image synthesizing means 40 by referring to the figures. Firstly, as shown in FIG. 5, the preprocessed shot images P1 to P3 are inputted to the marker detecting means 48 of the image processing means, and the marker detecting means 48 detects the positions where the dark lines D are inserted from the shot images P1 to P3. Now, using the thus detected positions of the dark lines D, the circumferential position aligning means 41A, as shown in FIG. 6, reads out the circumferential displacement angles α and β from the camera position storage means 44 and shifts the dark lines D of the shot images P1 and P3 in the circumferential direction by the numbers of shootings equivalent to the angles β and β relative to the dark line D of the shot image P2. Thus, the circumferential positions of the shot images are aligned, and the resulting data is outputted to the overlap synthesizing means 42.

Figure 7:
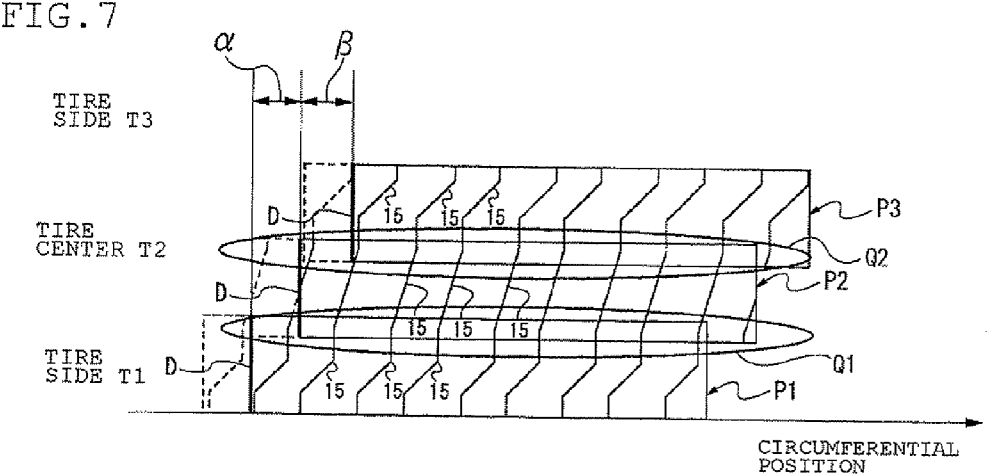
FIG. 7 is a conceptual diagram of synthesis of shot images by pattern matching in accordance with a first embodiment of the present invention.

Next, the overlap synthesizing means 42, as shown in FIG. 7, synthesizes the overlaps Q1 and Q2 through pattern matching of the shot image P1 with the shot image P2 and the shot image P2 with the shot image P3 using the periodically occurring protruding portions 15, called the ridges, which are found in the overlaps Q1 and Q2 of the shot images P1 to P3.

Figure 8:
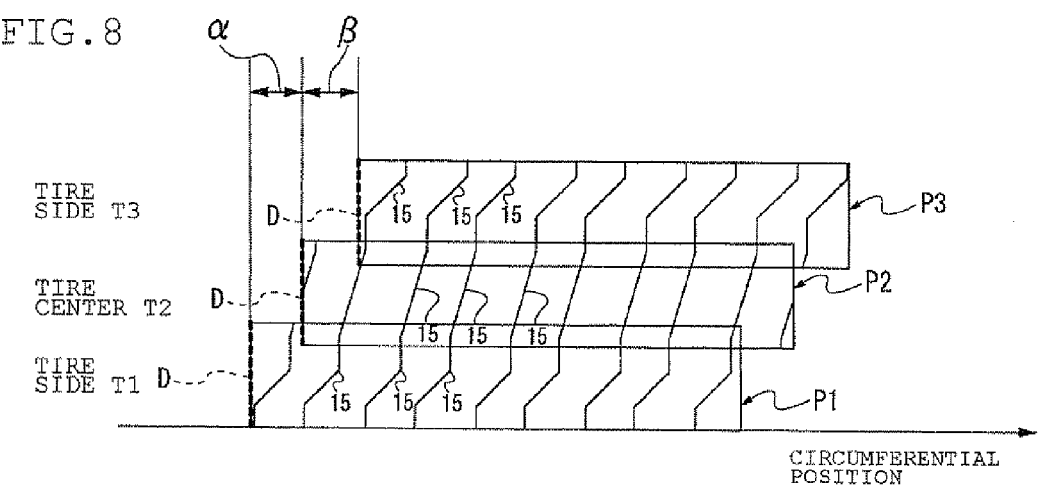
FIG. 8 is a processing diagram of image synthesis in accordance with a first embodiment of the present invention.
Figure 9:
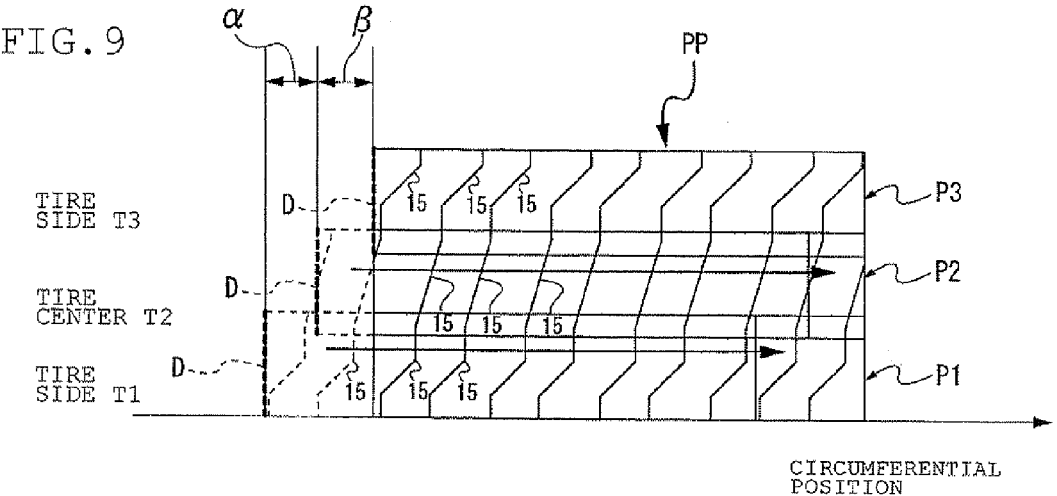
FIG. 9 is a processing diagram of image synthesis in accordance with a first embodiment of the present invention.

Then, the processing means 43, as shown in FIG. 8 and FIG. 9, performs a processing to make a synthesized image PP for a single tire by, for instance, deleting the dark lines D from the images synthesized by the overlap synthesizing means 42 and aligning one end of the images by moving the portions sticking out from the tire center T2, the tire side T1, and the tire side T3 to the other end thereof.

The synthesized image PP having been processed by the processing means 43 is outputted to the acceptability determining means 47 or the like, where the presence or absence of defects, such as molding marks or irregularities on the tire inner surface Ts resulting from the building process of the tire T, is determined from the surface unevenness. Then the result of this acceptability determination, together with the synthesized image PP, is displayed on the monitor 36 serving as the display means.

According to an inspection implementing the embodiment as described above, the images shot by the cameras 11 to 13 are aligned by correcting the circumferential displacements of the cameras 11 to 13 using the dark lines D as the markers which are inserted therein in the same timing. Therefore, the accuracy of synthesis of the shot images can be improved.

Second Embodiment

In the first embodiment, after the insertion of dark lines D as the markers by the marker inserting means 49, the numbers of shootings by the cameras 11 to 13 are reset, and the numbers of shootings thereby are counted again. However, the arrangement may be such that the rotation of the tire T is stopped at the insertion of the dark lines D.

More specifically, the marker inserting means 49 is connected to the laser beam generators 21 to 23 via a marker insertion line 74 and also to the motor drive means 51 via a temporary stop signal line. Thus, the arrangement is such that when the dark lines D are inserted by the laser beam generators 21 to 23, the rotation of the tire T is stopped temporarily for a time length equivalent to a single shooting.

In this case, the image shooting by the cameras 11 to 13 suffices if the number of shootings from the start of image shooting covers "number of shootings for full tire circle+one time of shooting". Note that the counting of the number of shootings in this embodiment is done as follows. Without any error in image shooting, the counting is finished when the count from the start of image shooting reaches the "number of shootings for full tire circle+one time of shooting". When any error in image shooting occurs, however, the count of the number of shootings by the camera having developed the error is reset once, and the counting performed again. At the same time, a reinsertion signal of dark lines D is outputted to the marker inserting means 49 to be discussed later. Accordingly, two or more dark lines D will be inserted during a single session of image shooting in the shot images of cameras without any error in image shooting. Hence, the number of shootings from the dark line D inserted before the dark line D inserted last is considered valid. For example, the image shooting is finished when the number of shootings from the dark line D inserted before the dark line D inserted last reaches the "number of shootings for full tire circle+one time of shooting".

Thus, as shown in FIGS. 10 to 13, the shot images P1 to P3 shot by the cameras 11 to 13 as described above can be processed into a synthesized image PP for full tire circle after they are subjected to an alignment of circumferential displacements using the dark lines D inserted therein as a reference and then a synthesis of the shot images through pattern matching thereof.

Also, according to the present embodiment, when an error during image shooting occurs as shown in FIG. 13 for instance, the inspection can be carried on as follows. Note that A2 in the figure refers to an image shooting time required for the "number of shootings for full tire circle+one time of shooting" and B1 to B3 refer to the preprocessing times.

Firstly, at time t0, the first tire T in this inspection begins rotating, and the cameras 11 to 13 start their image shooting. Since this is the initial image shooting for the first tire of the inspection, the image shootings of the respective regions, namely, the tire side T1, the tire center T2, and the tire side T3, are started simultaneously. With the start of these image shootings, the control means 46 starts counting the number of shootings by each of the cameras 11 to 13 individually. The image data obtained by the cameras 11 to 13 are successively outputted to the preprocessing means 31 to 33. And an annunciation signal indicating the image shooting in progress by each of the cameras 11 to 13 is outputted from the preprocessing means 31 to 33 to the control means 46.

Next, at time t1, based on the above annunciation signal, the marker inserting means 49 outputs a marker insertion signal to the laser beam generators 21 to 23 so that the slit lights 21a to 23a are turned off simultaneously for a time length equal to a single shooting. This results in an image of a pitch-dark marker of the same time, that is, a dark line D, within the images shot by the cameras 11 to 13.

Then, should an error in image shooting by the camera 11, for instance, occur at time E1, which is later than the time t1 when the dark line D is inserted, the camera 12 and the camera 13 in this embodiment will continue their image shooting. In this case, since the image shooting by the camera 11 must be performed from the beginning, the control means 46 performs the counting so that the number of shootings after the occurrence of the error in image shooting reaches the "number of shootings for full tire circle one time of shooting".

At time t2, recounting of the number of shootings by the camera 11 is performed by the control means 46. Thus, the control means 46 outputs a signal to cause the marker inserting means 49 to insert the dark lines D again in the shot images P1 to P3 shot by the cameras 11 to 13. The marker inserting means 49, in turn, outputs a marker insertion signal to the laser beam generators 21 to 23, so that the dark lines D are inserted in all of the images captured by the cameras 11 to 13. Due to this reinsertion of the dark lines D, correction is made to the counts of the shootings by the camera 12 and the camera 13 in such a manner that the number of shootings after the insertion of the dark line D at time t1 will eventually reach the "number of shootings for full tire circle+one time of shooting".

As a result, the image data obtained during the image shooting time F5 between time t0 and time t1 by the camera 12 and the camera 13 are overwritten with the image data obtained after the insertion of the second dark line D. And when the numbers of shootings by the cameras 12 and 13 reach the "number of shootings for full tire circle+one time of shooting", the image data are preprocessed by the preprocessing means 32 and 33, respectively.

Next, at time t3, when the number of shootings by the camera 11 shooting the tire side T1 reaches the "number of shootings for full tire circle+one time of shooting", all the image shooting of the first tire T comes to an end, and the preprocessing means 31 performs the preprocessing of the image data.

Next, at time t4, since the image shooting operation by all the cameras 11 to 13 is already finished, the second tire T to be inspected next is placed on the rotating table 53, and the start of image shooting is waited for.

Then, at time t5, when the preprocessing means 31 completes the preprocessing for the tire side T3 of the first tire in the preprocessing time B3, the preprocessing means 33 outputs an annunciation signal indicating the end of preprocessing to the control means 46. And the control means 46, based on this annunciation signal, causes not only the second tire T to rotate but also the camera 13 to start shooting the tire side T3 of the second tire, and starts counting the number of shootings. As the image data resulting from the start of image shooting by the camera 13 is outputted to the preprocessing means 33, the preprocessing means 33 outputs an annunciation signal indicating the shooting in progress by the camera 13 to the control means 46.

Next, the preprocessing means 31, when it completes the preprocessing for the tire side T1 of the first tire in the preprocessing time B1, outputs an annunciation signal indicating the end of preprocessing to the control means 46. The control means 46, in turn, causes the camera 11 to start shooting the tire side T1 of the second tire from an arbitrary position of the rotating tire T and starts counting the number of shootings. As the image data resulting from the start of image shooting by the camera 11 is outputted to the preprocessing means 31, the preprocessing means 31 outputs an annunciation signal indicating the shooting in progress by the camera 11 to the control means 46.

Next, the preprocessing means 32, when it completes the preprocessing for the tire center T2 of the first tire in the preprocessing time B2, outputs an annunciation signal indicating the end of preprocessing to the control means 46. The control means 46, in turn, causes the camera 12 to start shooting the tire center T2 of the second tire from an arbitrary position of the rotating tire T and starts counting the number of shootings. As the image data resulting from the start of image shooting by the camera 12 is outputted to the preprocessing means 32, the preprocessing means 32 outputs an annunciation signal indicating the shooting in progress by the camera 12 to the control means 46. With this annunciation signal from the preprocessing means 32 inputted to the control means 46, the control means 46 is notified of the fact that the image shooting of the second tire T by all of the cameras 11 to 13 has started.

Next, at time t6, based on the above annunciation signal, the marker inserting means 49 outputs a marker insertion signal to the laser beam generators 21 to 23 so that the slit lights 21a to 23a are turned off simultaneously for a time length equal to a single shooting. This results in an image of a dark line D as the marker of the same time within each of the images shot by the cameras 11 to 13.

Thus, by repeating the above-described processes, the inspection of the tire T, which comes successively on a conveyor, can be accomplished with great efficiency.

By implementing the arrangement as described above, the waiting times C1 and C2 which existed with the cameras 11 and 13 shooting the tire sides T1 and T3 in the conventional technology can be eliminated. Also, the timings, in which the preprocessed shot images for the respective regions of the tire sides T1 and T3 and the tire center T2 are outputted, can be gradually shifted by providing time differences for the time of start or end of preprocessing. Therefore, smooth transfer of images can be achieved by avoiding collisions in the transfer of images outputted from the preprocessing means 31 to 33 to the control means 46. Also, in the same way as in the first embodiment, accurate alignment can be accomplished because the shot images are aligned with each other using dark lines D, which are the markers, as a reference.

As thus far explained in the first embodiment and the second embodiment, according to the present invention, dark lines D are inserted as markers at the same time in the images shot by the cameras 11 to 13. Accordingly, it is possible to control the image shooting operations of the cameras 11 to 13 individually. For example, the waiting times C1 and C2 for the shot images, which can occur due to the differences in the preprocessing time after the image shooting, can be reduced.

Also, in the synthesis of the shot images captured by all of the cameras 11 to 13, the circumferential positions of the cameras are aligned in accordance with the relative displacement angles α and β in the circumferential direction between the cameras, i.e., between the cameras 11 and 12 and between the cameras 12 and 13, using the dark lines D in the shot images. This results in an enhanced accuracy of position alignment of the shot images P1 to P3. Further, because of the improved accuracy of position alignment, the matching accuracy will also be improved when the shot images are pattern-matched with each other. This will prevent erroneous determination of conforming articles as non-conforming ones attributable to faulty image analysis.

In the foregoing description, the marker inserting means 49 of the control means 46 inserts dark lines D as markers in the images shot by the cameras 11 to 13 by causing the slit lights 21a to 23a to stop their illumination temporarily for a time length equivalent to a single shooting. Yet, the arrangement may be such that the luminance is raised, contrary to the dark line D, so that the illuminated portion becomes sufficiently brighter than the other portions of the shot image.

Also, the arrangement may be such that synchronized markers are inserted in the images outputted by the cameras 11 to 13 to the preprocessing means 31 to 33 through some processing by the preprocessing means, instead of actually changing the luminance of the slit lights 21a to 23a. Furthermore, noise as the marker may be inserted in the images by adding some other arrangement. More specifically, a marker may be inserted by use of an ultrasonic generator, an ultraviolet generator, or a high-voltage generator. Moreover, the marker may consist of a plurality of lines.

Also, the arrangement described is such that the tire T, which is the object to be inspected, is rotated simultaneously with the beginning of image shooting. However, the arrangement may be such that the tire T is rotated as soon as it is placed on the rotating table 53, and the image shooting is started at an arbitrary position on the rotating tire T.

Also, the description of the image shooting in the inspection has been such that the number of shootings for full tire circle is counted using the slit width 51 of a slit light as a reference. However, the arrangement may be such that the length of full tire circle is determined using the number of camera pixels and the number of shootings is obtained accordingly.

Although the foregoing description has been of the inner surface inspection of the tire, the present invention can be applied to the outer surface inspection of the tire also. Further, the method of this invention can be applied to the synthesis processing of images shot by a plurality of cameras in other inspections. According to the present invention, the inspection can be performed with great efficiency because an accurate synthesis can be accomplished through position alignment of the images with each other and a plurality of cameras, which are the image shooting means, can be operated individually.

DESCRIPTION OF REFERENCE NUMERALS

11; 12; 13 camera
21; 22; 23 laser beam generator
21a; 22a; 23a slit light
31; 32; 33 preprocessing means
40 synthesizing means
41; 41A circumferential position aligning means
42 overlap synthesizing means
43 processing means
44 camera position storage means
46 control means
47 acceptability determining means
48 marker detecting means
49 marker inserting means
51 motor drive means
D dark line
P1 to P3 image shot image
T tire
T1; T3 tire side
T2 tire center
Ts tire inner surface

The invention claimed is:

1. An apparatus for inspecting a tire, comprising:
a plurality of image shooting means located at positions relatively displaced in a circumferential direction so as to shoot images of the circumferential surface of the tire and set for the respective shooting positions different from each other in an axial direction of the tire;
a marker inserting means for entering markers in the images shot by all of the image shooting means at the same time when image shooting is being performed by all of the image shooting means while the tire is rotated circumferentially relative to the plurality of image shooting means; and
an image synthesizing means for synthesizing the images shot by all of the image shooting means by shifting the markers in accordance with a relative displacements in the circumferential direction of the respective image shooting means.

2. The apparatus for inspecting a tire as recited in claim 1, wherein an image shooting operation of the image shooting means is started one after the other as an image data processing operation after an image shooting operation is finished.

3. The apparatus for inspecting a tire as recited in claim 1, wherein an image shooting operation of the image shooting means is started in timings different for the respective image shooting means.

4. The apparatus for inspecting a tire as recited in claim 1, wherein changing of the tire to be inspected is performed after a completion of image shooting operation by all of the image shooting means.

5. The apparatus for inspecting a tire as recited in claim 1, wherein the marker inserting means causes a change in luminance of an illuminating means illuminating the shooting positions of the respective image shooting means.

6. The apparatus for inspecting a tire as recited in claim 1, wherein the marker inserting means creates noise in the images shot by the respective image shooting means.

7. The apparatus for inspecting a tire as recited in claim 1, wherein each of the markers inserted by the marker inserting means consists of a plurality of lines.

8. The apparatus for inspecting a tire as recited in claim 1, wherein the image shooting means perform image shootings of a circumferential surface of the tire for full circle and an image shooting of a marker inserted only.

9. The apparatus for inspecting a tire as recited in claim 1, wherein the plurality of image shooting means are so set as to shoot a respectively different regions of a tire circumferential surface and the image shooting means shooting a neighboring regions shoot images so as to have overlaps of the regions, so that the images can be synthesized by performing pattern matching of the overlaps of the images shot.

* * * * *